United States Patent [19]
Hydeman et al.

[11] Patent Number: 5,675,096
[45] Date of Patent: Oct. 7, 1997

[54] APPARATUS AND METHOD FOR REMOVING A WALL PORTION FROM A WALL OF A TUBULAR MEMBER

[75] Inventors: Jeffrey E. Hydeman, Murrysville; William G. Cole, Greensburg; Stephen M. Ira, Pittsburgh, all of Pa.

[73] Assignee: Westinghouse Electric Corporation, Pittsburgh, Pa.

[21] Appl. No.: 355,583

[22] Filed: Dec. 14, 1994

[51] Int. Cl.$^6$ .................................................. G01N 3/28
[52] U.S. Cl. .................. 73/864.41; 83/919; 83/178
[58] Field of Search .......................... 73/864.41, 864.42, 73/865.8, 86; 83/54, 110, 150, 151, 153, 178, 180, 188, 919; 30/92, 103, 104, 108, 124; 376/245, 249, 258

[56] References Cited

U.S. PATENT DOCUMENTS

| | | | |
|---|---|---|---|
| 3,628,246 | 12/1971 | Bronne et al. | |
| 3,675,494 | 7/1972 | Becque | |
| 4,438,805 | 3/1984 | Gugel | 165/76 |
| 4,466,185 | 8/1984 | Montiero | |
| 4,710,710 | 12/1987 | Flora et al. | 324/220 |
| 4,773,799 | 9/1988 | Guironnet | |
| 4,788,026 | 11/1988 | Widener | 376/245 |

FOREIGN PATENT DOCUMENTS

| | | | |
|---|---|---|---|
| 8806722 | 9/1988 | WIPO | 83/919 |

*Primary Examiner*—Robert Raevis

[57] ABSTRACT

Apparatus and method for removing a wall portion from a wall of a tubular member. The wall portion has a distal end portion and a proximal end portion. The wall portion is connected to the wall of the tubular member by a pair of ligatures, which remain after use of a suitable cutting tool. The ligatures are aligned and disposed on either side of the wall portion to define a pivot axis. The apparatus has a probe body insertable into the tubular member, which probe body includes an expandable bladder for pushing the distal end portion of the wall portion in order to pivot the wall portion about the ligatures (i.e., about the pivot axis) as the bladder expands. As the wall portion pivots, the distal end portion of the wall portion rotates outwardly from the wall of the tubular member as the proximal end portion of the wall portion rotates inwardly into the tubular member. After the wall portion pivots, a cup-shaped retainer is moved upwardly to surround the proximal end portion of the wall portion. A movable elongate mandrel engages the proximal end portion of the wall portion. A hydraulic or pneumatic cylinder downwardly moves the mandrel in order to intimately engage the mandrel with the proximal end portion of the wall portion and downwardly displace the wall portion, such that the ligatures are severed. As the wall portion is downwardly displaced, it is drawn into the retainer. As the wall portion is drawn into the retainer, it is gripped between the retainer and the mandrel. The probe body is then removed from the tubular member for removing the severed wall portion from the tubular member. The apparatus may further include an eddy current sensor for locating the wall portion to be removed.

23 Claims, 13 Drawing Sheets

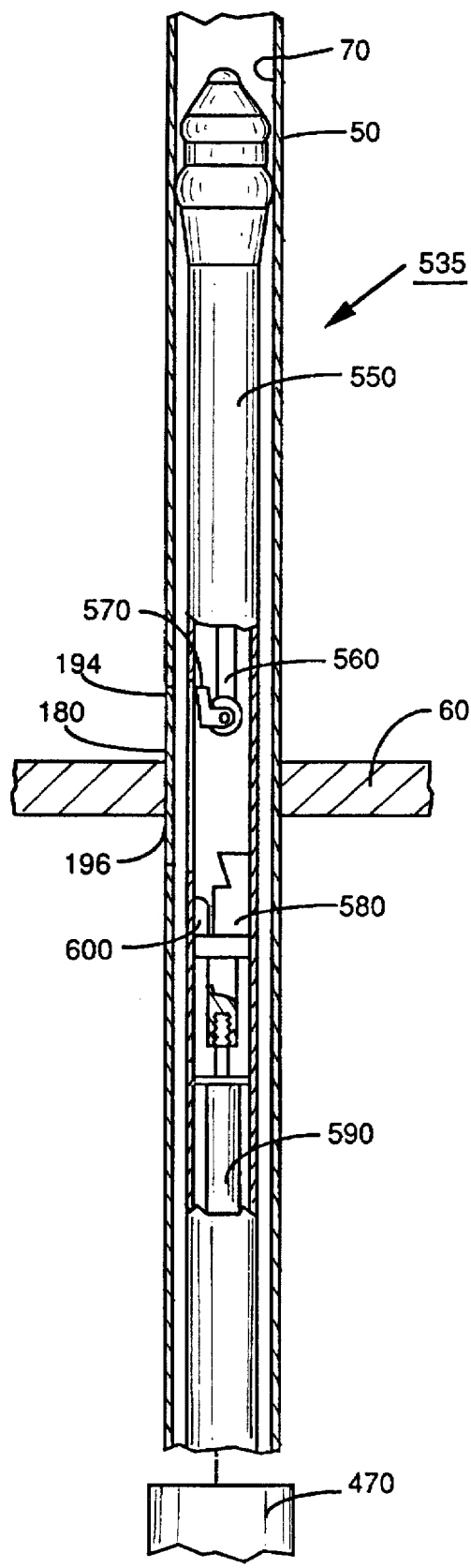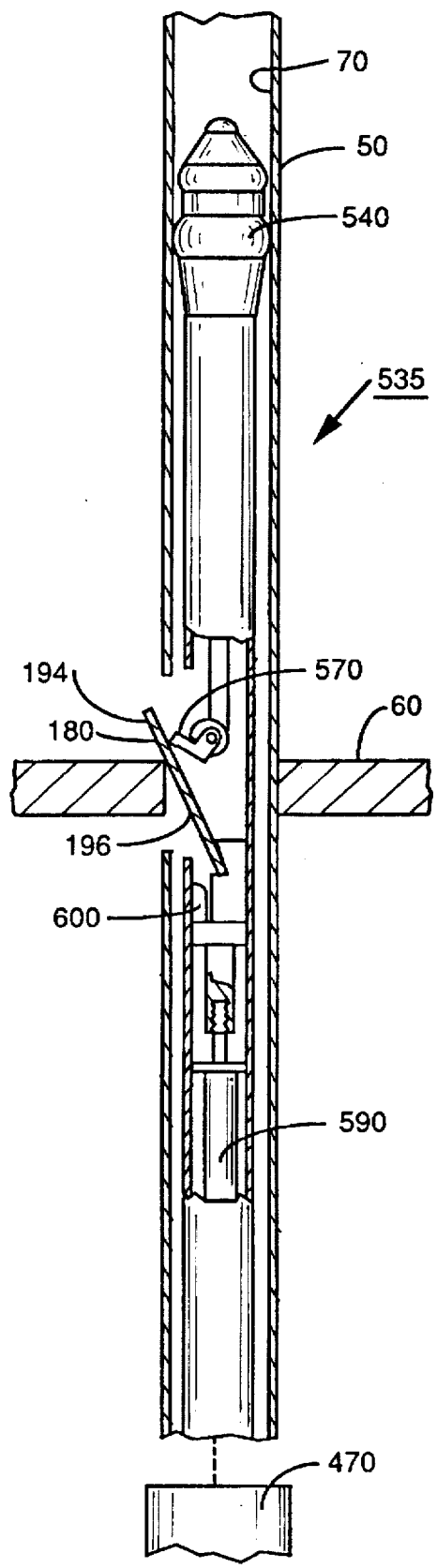

APPARATUS AND METHOD FOR REMOVING A WALL PORTION FROM A WALL OF A TUBULAR MEMBER

BACKGROUND OF THE INVENTION

This invention generally relates to apparatus and methods for obtaining samples for analysis and more particularly relates to an apparatus and method for removing a wall portion from a wall of a tubular member, such as a nuclear steam generator tube, so that the tubing material thereof may be analyzed.

It is well known that a typical nuclear steam generator or heat exchanger generates steam when heat is transferred from a heated and radioactive primary fluid to a nonradioactive secondary fluid of lower temperature. In order to accomplish the heat transfer, the secondary fluid surrounds a plurality of leak-tight heat transfer tubes disposed in the steam generator as the primary fluid flows through the tubes.

Occasionally, however, the steam generator tubes may experience tube wall cracking and thus may not remain leak-tight. If through-wall cracking occurs, the radioactive primary fluid may leak through the cracks and commingle with the nonradioactive secondary fluid, a highly undesirable result. Therefore, the tubing material is periodically sampled and analyzed in order to determine whether tube wall cracking is eminent.

One prior art method of obtaining the necessary samples is to "pull" or extract one or more of the tubes in order perform analyses thereon. The tube "pull" process includes heating the tube to relax the tube, cutting away a section of the tube from the inside thereof, pulling the severed tube section through the tubesheet hole as segments of the severed tube section are progressively cutting-off, and installing a plug in the now empty tubesheet hole formally occupied by the tube. This process may be repeated for each leg of the U-shaped tube.

However, applicants have observed that the tube pull process is time consuming because it requires up to approximately 24 hours per tube to complete. Thus, the time required to perform the tube pull process may undesirably extend plant outages and may increase radiation exposure to service personnel performing the "tube pull". It is important to avoid an extended plant outage because such an extended outage may result in approximately $300,000 per day in replacement power costs to the reactor owner. Also, it is important to avoid increased radiation exposure to service personnel because U.S. Government regulations require radiation exposure to be held to a level that is as low as reasonably achievable.

Hence, there has been a long felt need in the industry to provide an apparatus and method for sampling the tubes that is not time consuming, does not result in extended plant outages and does not increase radiation exposure to service personnel. Therefore, such an apparatus and method preferably should be capable of sampling the tube without the time-consuming need to "pull" the tube.

Therefore, what is needed are an apparatus and method for removing a wall portion from a wall of a tubular member, such as a nuclear steam generator heat transfer tube, so that the tubing material thereof may be analyzed.

SUMMARY OF THE INVENTION

Disclosed herein are an apparatus and method for removing a wall portion from a wall of a tubular member. The wall portion has a distal end portion and a proximal end portion. The wall portion is connected to the wall of the tubular member by a pair of ligatures, which remain after use of a suitable cutting tool. The ligatures are aligned and disposed on either side of the wall portion to define hinges aligned along a pivot axis. The apparatus has a probe body insertable into the tubular member, which probe body includes an expandable bladder for pushing the distal end portion of the wall portion in order to pivot the wall portion about the ligatures (i.e., about the pivot axis) as the bladder expands. As the wall portion pivots, the distal end portion of the wall portion rotates outwardly from the wall of the tubular member as the proximal end portion of the wall portion rotates inwardly into the tubular member. After the wall portion pivots, a cup-shaped retainer is moved upwardly to surround the proximal end portion of the wall portion. A movable elongate mandrel then engages the proximal end portion of the wall portion. In this regard, a hydraulic or pneumatic cylinder downwardly moves the mandrel in order to intimately engage the mandrel with the proximal end portion of the wall portion and then downwardly displace the wall portion, such that the ligatures are severed. As the wall portion is downwardly displaced, it is drawn into the retainer. As the wall portion is drawn into the retainer, it is gripped between the retainer and the mandrel. The probe body is then removed from the tubular member for removing the severed wall portion from the tubular member. The apparatus may further include an eddy current sensor for locating the wall portion to be removed.

The invention in its broad form is an apparatus for removing a wall portion from a wall of a tubular member, the wall portion suspended in the wall of the tubular member by a ligature thereof, comprising displacement means for displacing the wall portion, so that the ligature severs as the wall portion is displaced; and retaining means disposed adjacent said displacement means for retaining the wall portion as the ligature severs.

The invention in its broad form is also a method of removing a wall portion from a wall of a tubular member, the wall portion suspended in the wall of the tubular member by a ligature thereof, comprising the steps of displacing the wall portion, so that the ligature severs as the wall portion is displaced; and retaining the wall portion as the ligature severs.

An object of the present invention is to provide an apparatus and method for removing a wall portion cut from a wall of a tubular member, the cut wall portion remaining attached to the wall of the tubular member only by a ligature thereof.

A feature of the present invention is the provision of displacement means for displacing the wall portion, so that the ligature severs as the wall portion is displaced.

Another feature of the present invention is the provision of retaining means disposed adjacent the displacement means for retaining the wall portion as the ligature severs, so that the wall portion can then be removed from the tubular member for later analysis.

An advantage of the present invention is that the wall portion may be removed from the wall of the tubular member in a manner that is less time consuming than the prior art tube "pull" process, that does not result in extended plant outages and that does not increase radiation exposure to service personnel.

Another advantage of the present invention is that the opening left in the wall of the tubular member after removal of the wall portion affords a vantage point to visually inspect the condition of neighboring tubular members.

These and other objects, features and advantages of the present invention will become apparent to those skilled in the art upon a reading of the following detailed description when taken in conjunction with the drawings wherein there is shown and described illustrative embodiments of the invention.

BRIEF DESCRIPTION OF THE DRAWINGS

While the specification concludes with claims particularly pointing out and distinctly claiming the subject matter of the present invention, it is believed the invention will be better understood from the following description taken in conjunction with the accompanying drawings wherein:

FIG. 15 is a view in partial vertical section of an alternative embodiment of the invention disposed in operative condition to pivot the wall portion;

FIG. 16 is a view in partial vertical section of the alternative embodiment of the invention pivoting the wall portion.

DESCRIPTION OF THE PREFERRED EMBODIMENTS

Figure 1:
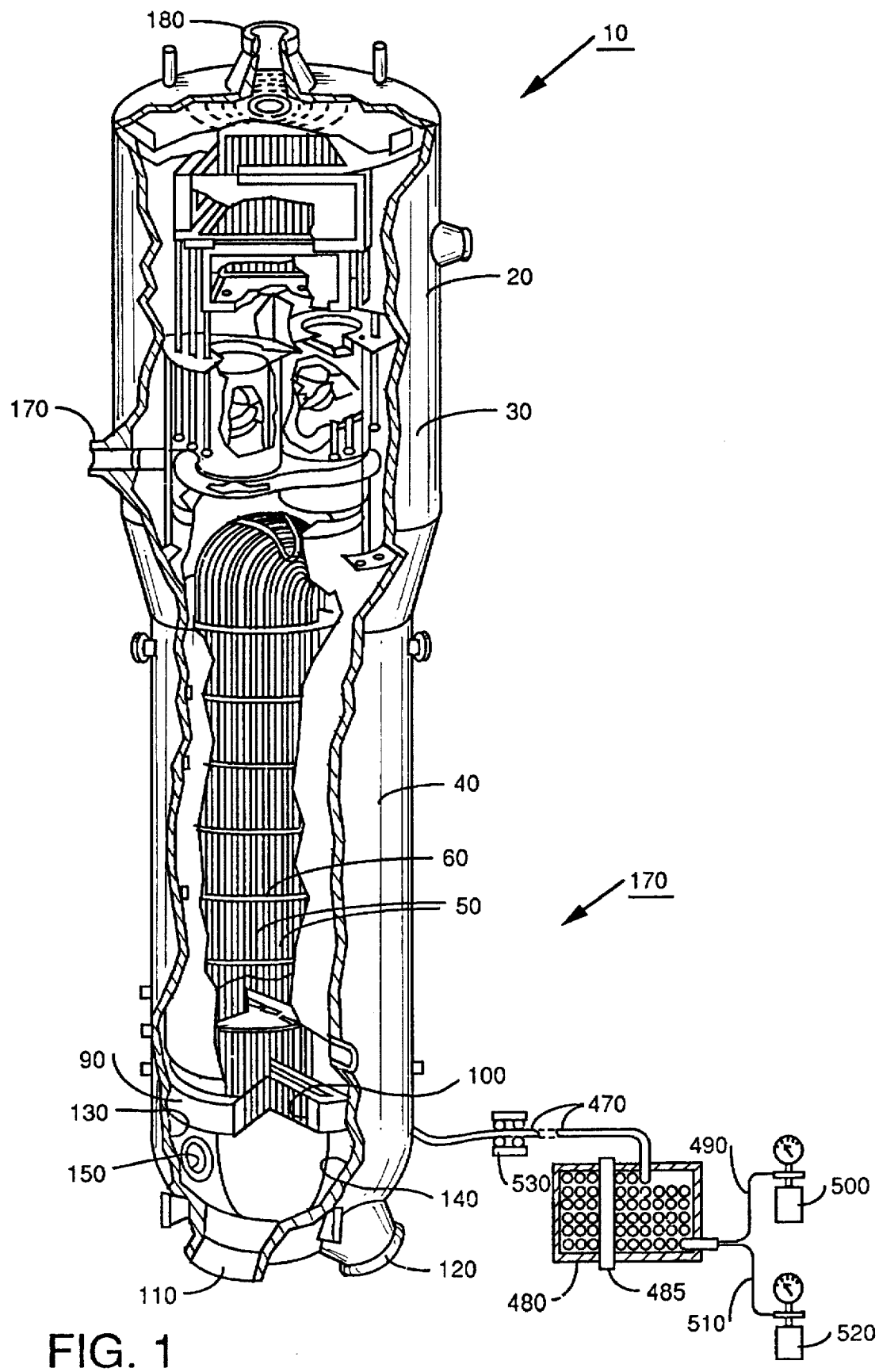
FIG. 1 is a perspective view in partial vertical section of a typical nuclear steam generator with parts removed for clarity, the steam generator having a plurality of U-shaped heat transfer tubes disposed therein.

Referring to FIG. 1, there is shown a typical nuclear steam generator or heat exchanger, generally referred to as 10, for generating steam. Steam generator 10 comprises a shell 20 having an upper portion 30 and a lower portion 40. Disposed in lower portion 40 are a plurality of inverted U-shaped heat transfer tubes 50 that extend through respective ones of a plurality of holes 55 (see FIG. 2) formed through each of a plurality of horizontal support plates 60. Each tube 50 is leak-tight and has an inner surface 70 and a pair of tube ends 80 (see FIG. 2). As shown in FIG. 1, disposed in lower portion 40 is a tubesheet 90 having holes 100 therethrough for receiving tube ends 80. Attached to shell 20 are a first inlet nozzle 110 and a first outlet nozzle 120 in fluid communication with an inlet plenum chamber 130 and with an outlet plenum chamber 140, respectively. A plurality of manway holes 150 are formed through shell 20 below tubesheet 90 for allowing access to inlet plenum chamber 130 and outlet plenum chamber 140. Moreover, attached to shell 20 above tubesheet 90 is a second inlet nozzle 160 for entry of a non-radioactive secondary fluid into shell 20. A second outlet nozzle 170 is attached to the top of upper portion 30 for exit of steam from steam generator 10.

During operation of steam generator 10, radioactive primary fluid heated by a nuclear reactor core (not shown) enters inlet plenum chamber 130 through first inlet nozzle 110 and flows through tubes 50 to outlet plenum chamber 140 where the primary fluid exits steam generator 10 through first outlet nozzle 120. As the primary fluid enters inlet plenum chamber 130, the secondary fluid simultaneously enters second inlet nozzle 160 to ultimately surround tubes 50, such that a portion of this secondary fluid vaporizes to steam due to conductive heat transfer from the primary fluid flowing through tubes 50 to the secondary fluid surrounding tubes 50. The steam exits steam generator 10 through second outlet nozzle 170 and is conducted to a turbine-generator set (not shown) for producing electricity in a manner well known in the art.

Occasionally, however, steam generator tubes 50 may experience tube wall cracking and thus may not remain leak-tight. If through-wall cracking occurs, the radioactive primary fluid may leak through the cracks and commingle with the nonradioactive secondary fluid, a highly undesirable result. Hence, it is desirable to periodically extract samples of the tubing material comprising tubes 50 in order to establish the condition (e.g., whether tube wall cracking is eminent) of tubes 50 by appropriate analysis.

Figure 2:
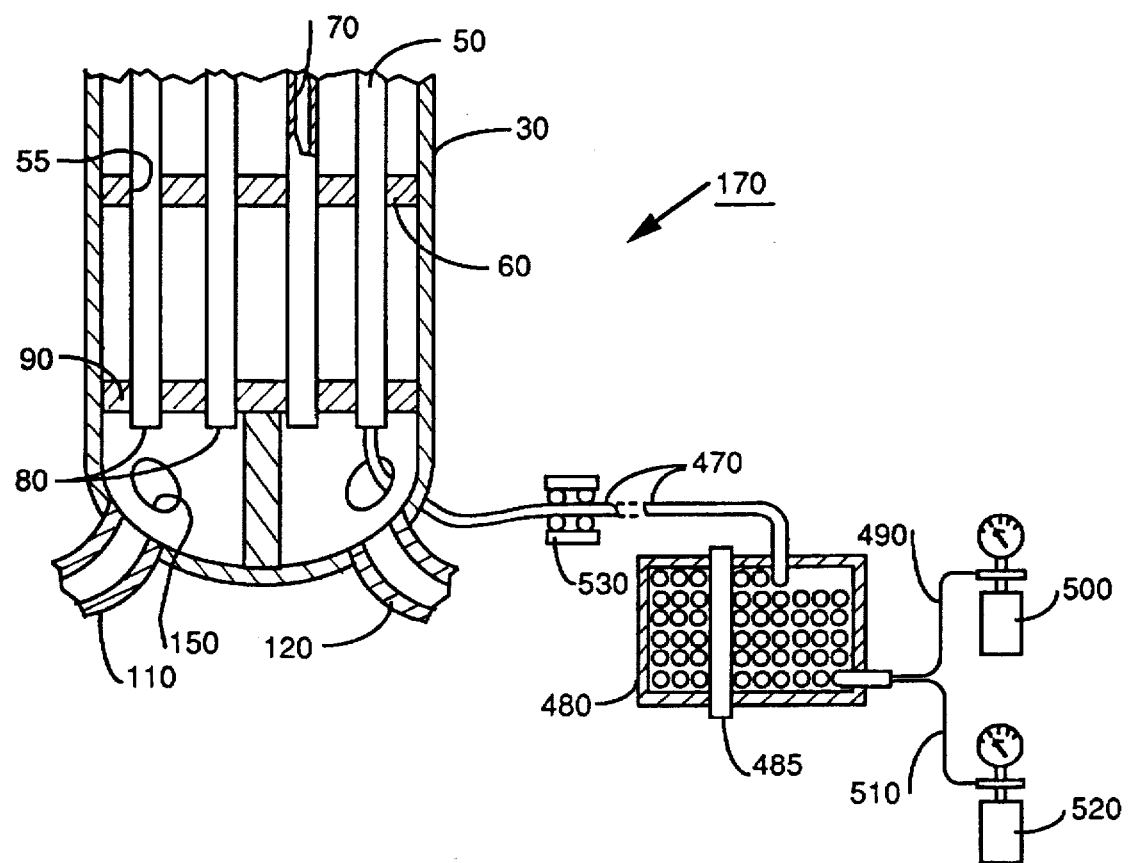
FIG. 2 is a view in vertical section of a lower portion of the steam generator, this view also showing the invention inserted into a selected one of the heat transfer tubes for removing a wall portion therefrom.
Figure 3:
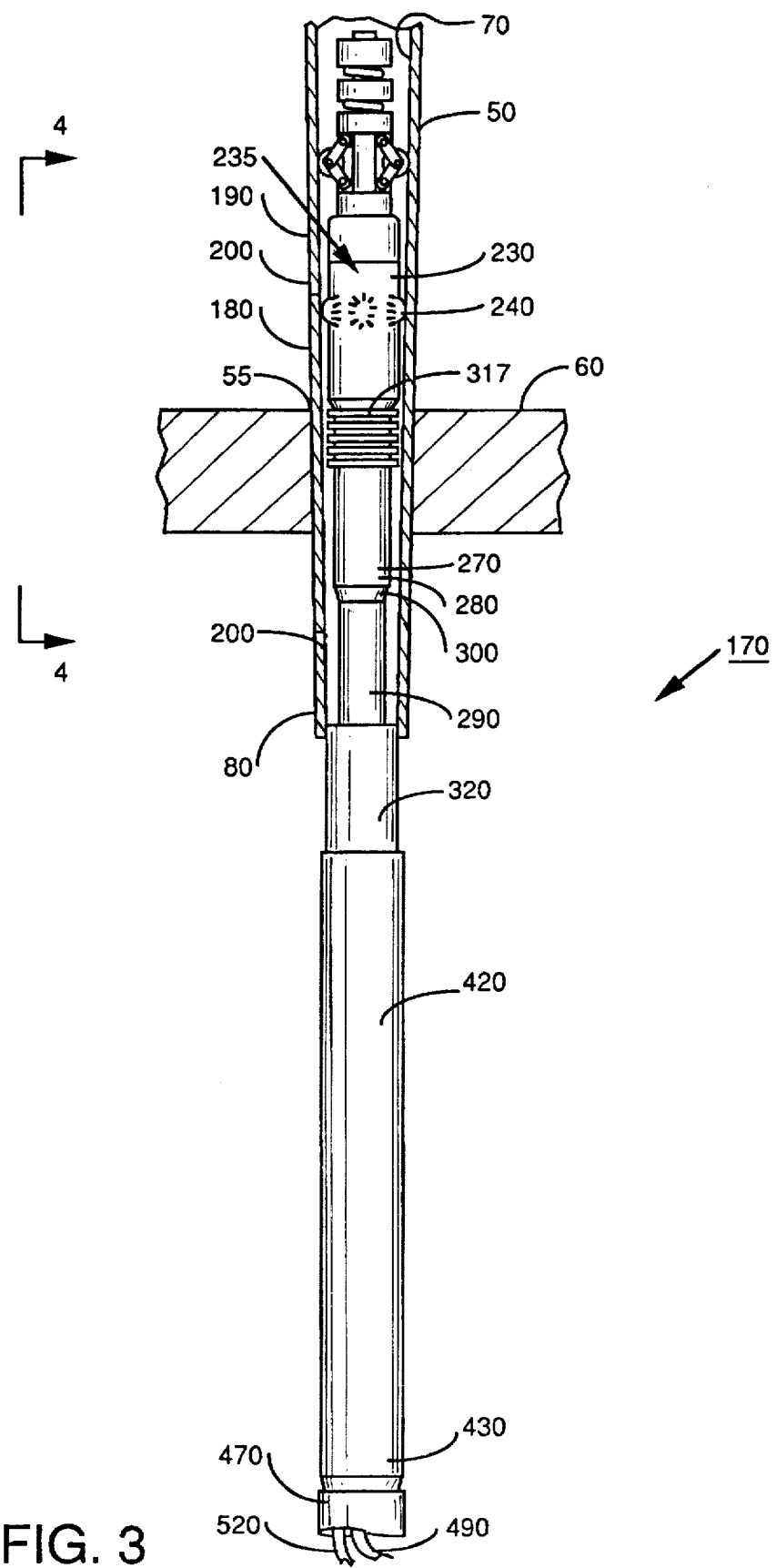
FIG. 3 is a view in full elevation of the invention disposed in the tube for removing the wall portion.
Figure 4:
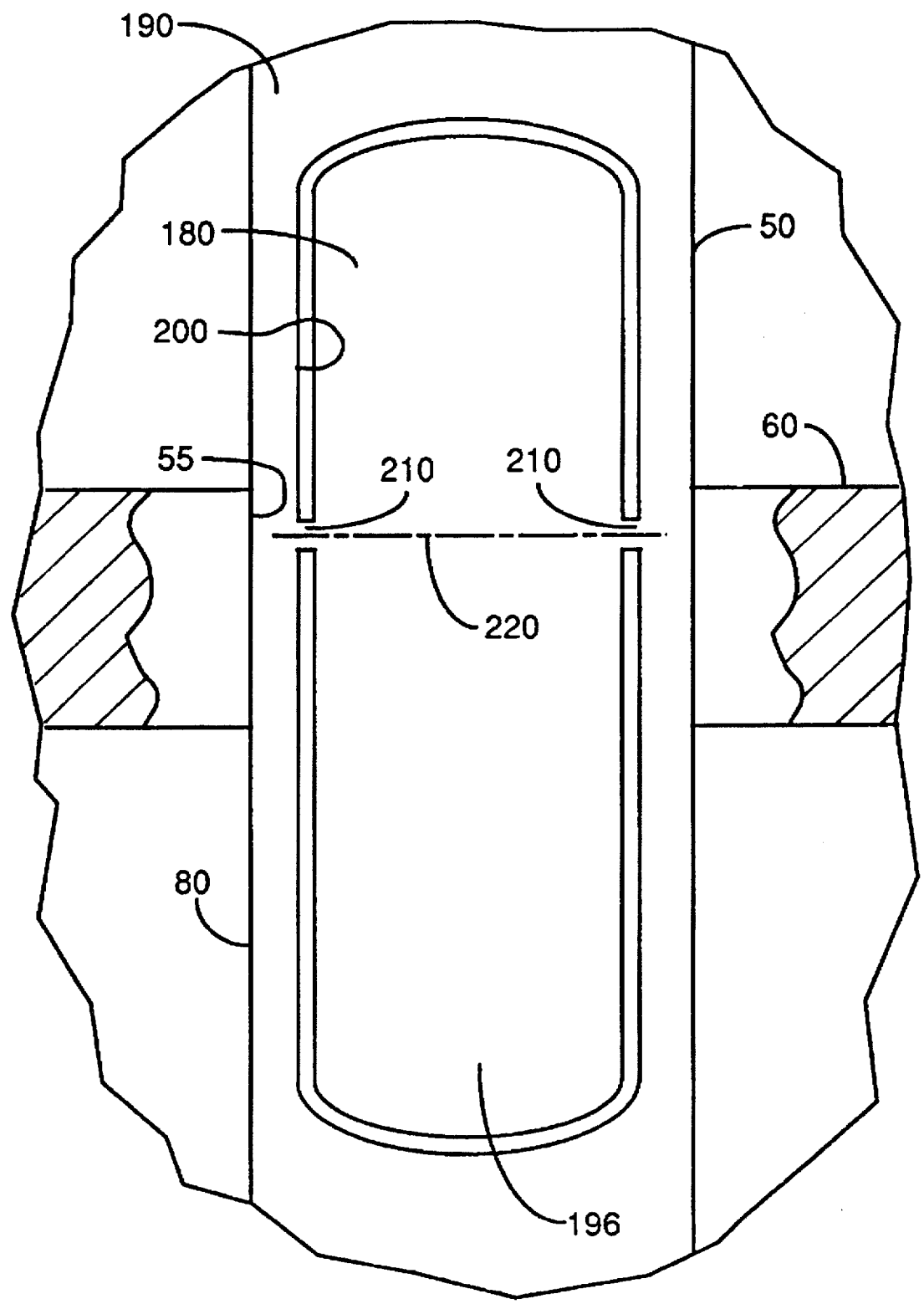
FIG. 4 is a view along section line 4—4 of FIG. 3 showing the wall portion being retained in the wall of the tube only by a pair of ligatures connecting the wall portion to the wall of the tube.
Figure 5:
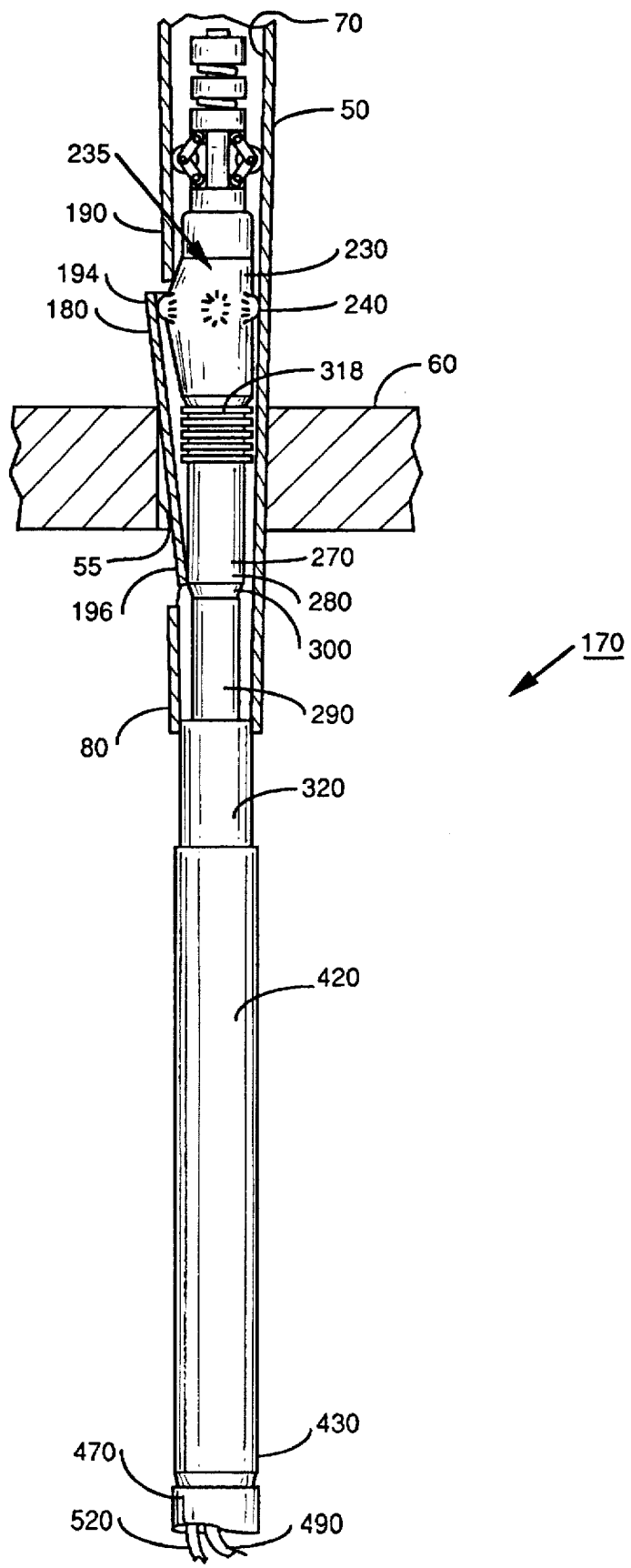
FIG. 5 is a view in full elevation of the invention tilting or pivoting the wall portion about the ligatures, so that the wall portion can be properly positioned to allow it to be severed from the wall of the tube.
Figure 6:
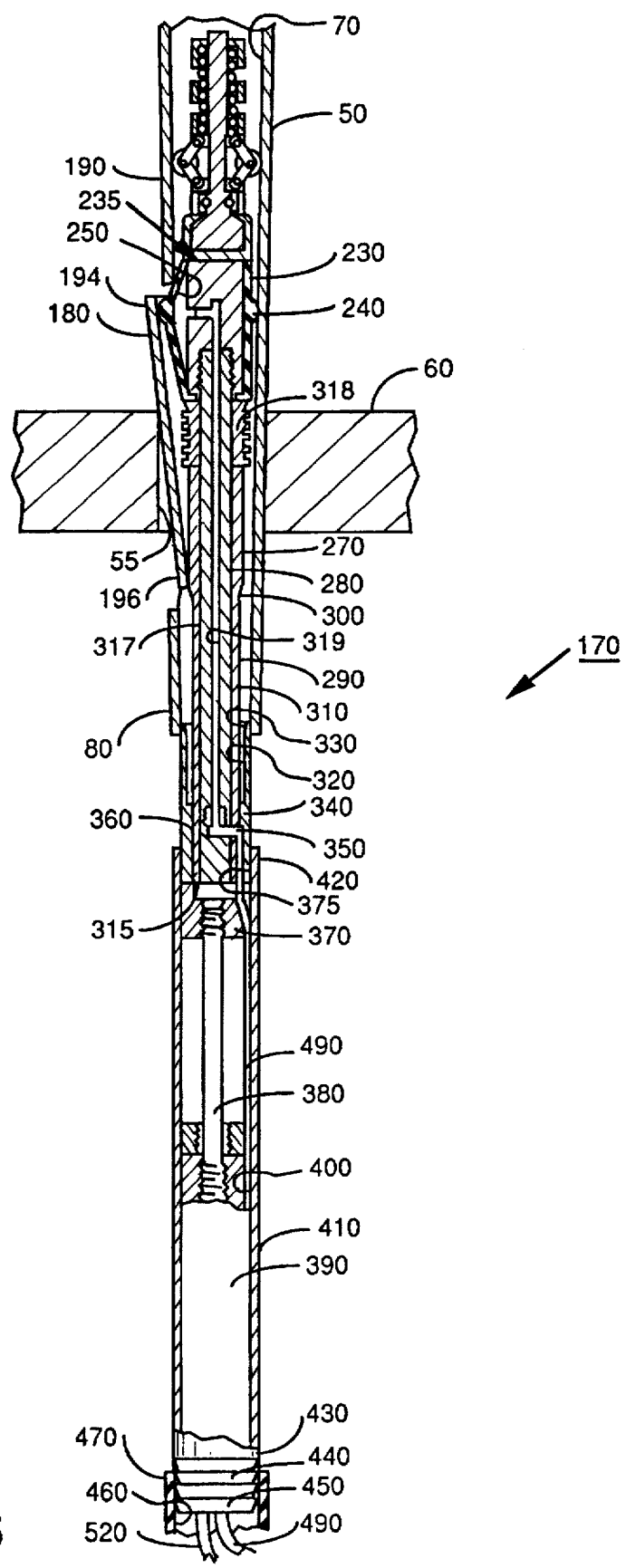
FIG. 6 is a view in partial vertical section of the invention tilting or pivoting the wall portion about the ligatures, so that the wall portion can be properly positioned to allow it to be severed from the wall of the tube.
Figure 7:
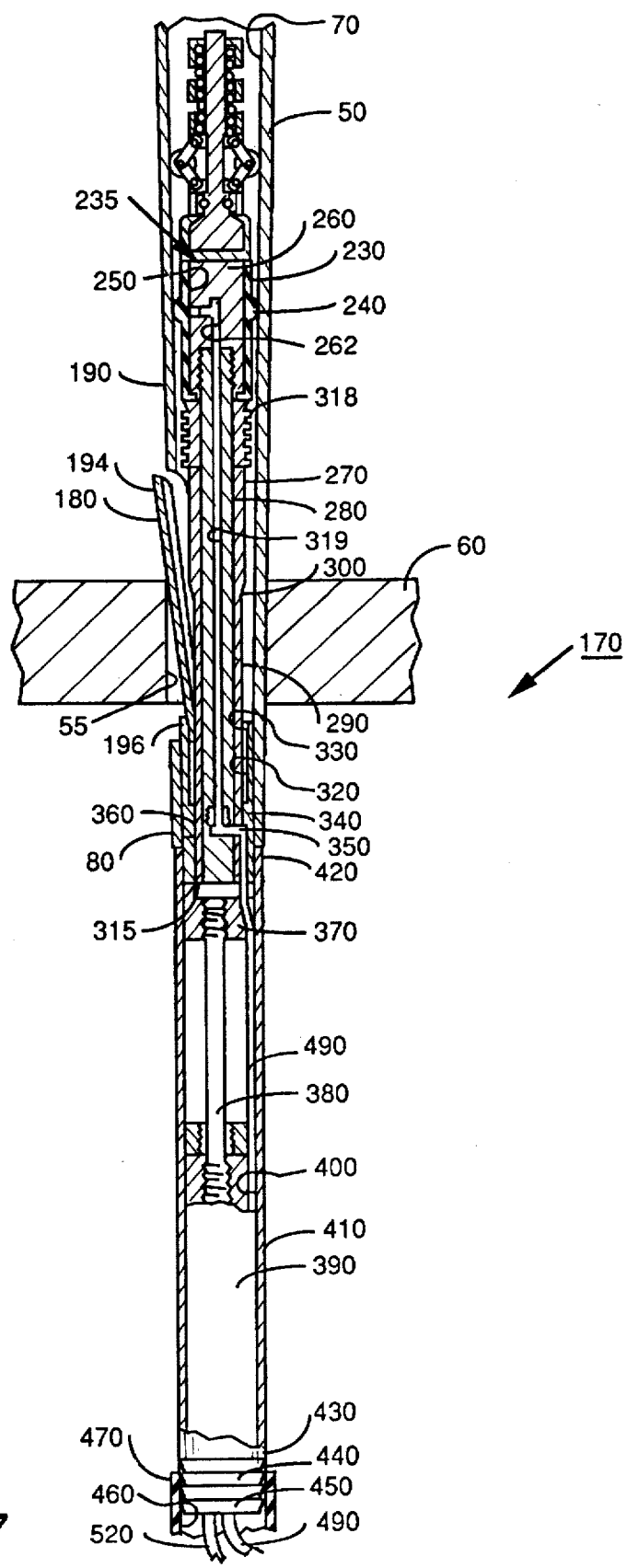
FIG. 7 is a view in partial vertical section of the invention showing a cup-shaped retainer coacting with an elongate mandrel for retaining or gripping the wall portion therebetween as the ligatures and thus the wall portion are severed from the wall of the tube as the mandrel is downwardly moved, the wall portion being shown only partially retained or gripped between the mandrel and the retainer.
Figure 8:
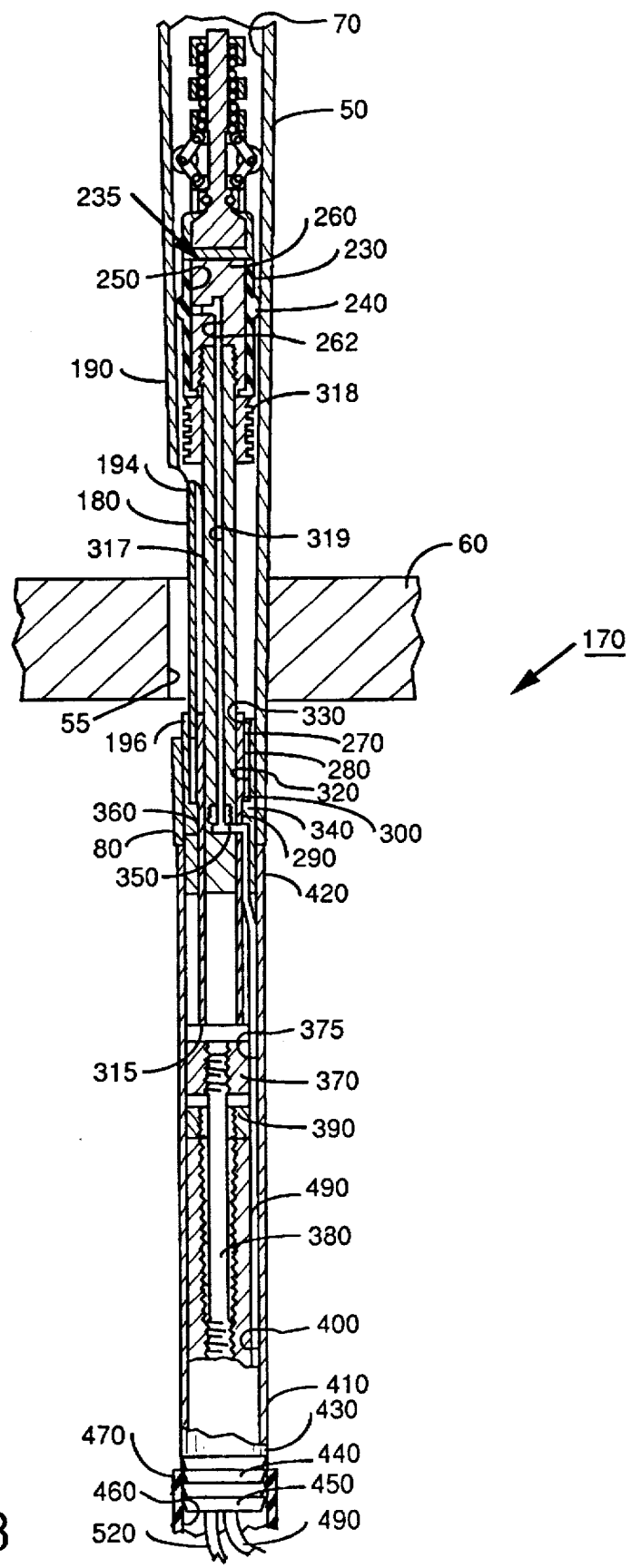
FIG. 8 is a view in partial vertical section of the invention showing the severed wall portion fully retained or gripped between the mandrel and the retainer.
Figures 9, 10:
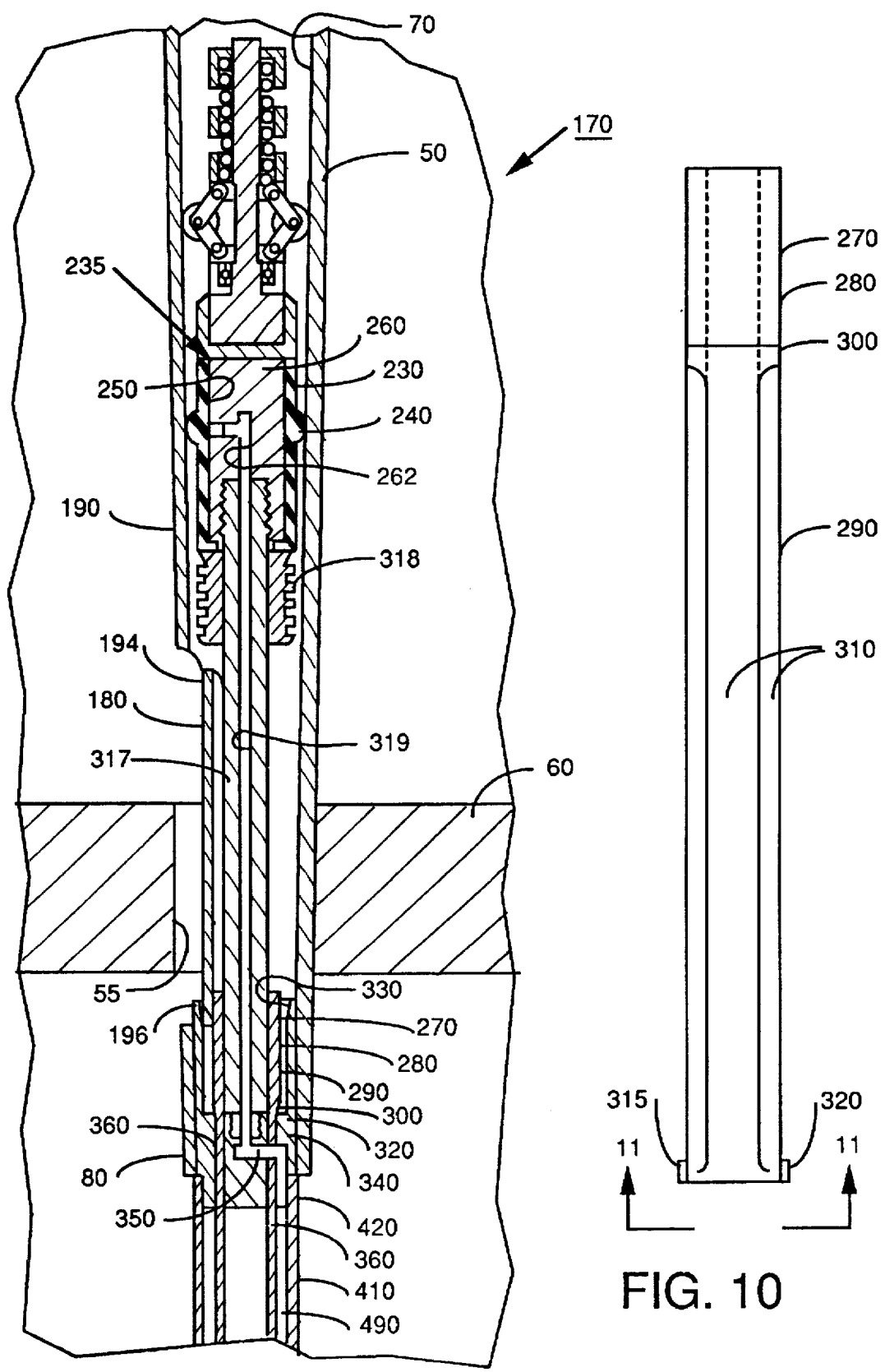
FIG. 9 is a fragmentation view in vertical section of the invention showing the severed wall portion fully retained or gripped between the mandrel and the retainer.
FIG. 10 is a view in full elevation of the mandrel.
Figure 11:
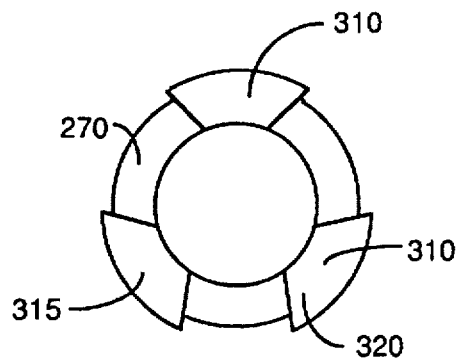
FIG. 11 is a view along section line 11—11 of FIG. 10.
Figure 12:
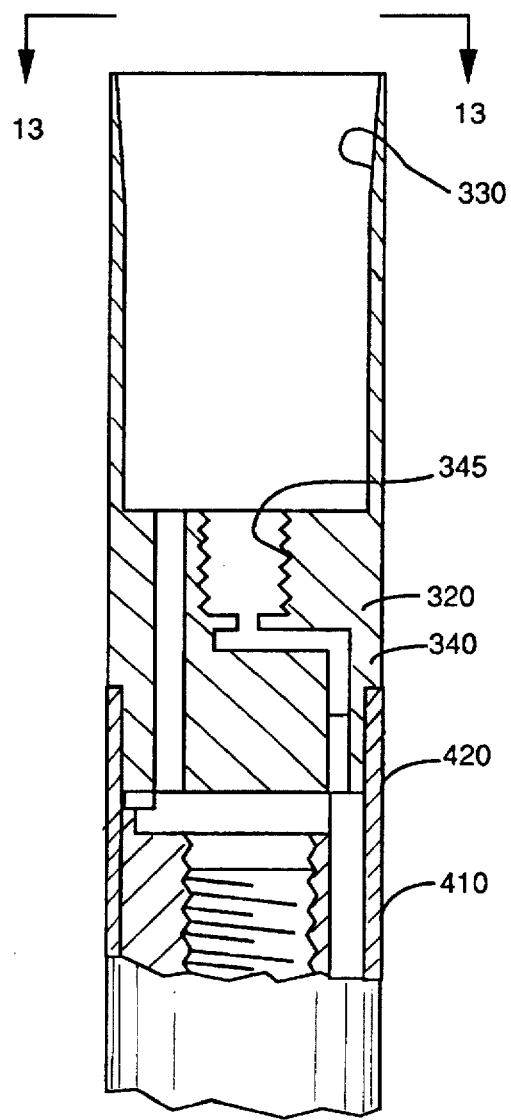
FIG. 12 is a view in vertical section of the retainer which retains the wall portion after the wall portion severs from the wall of the tube.
Figure 13:
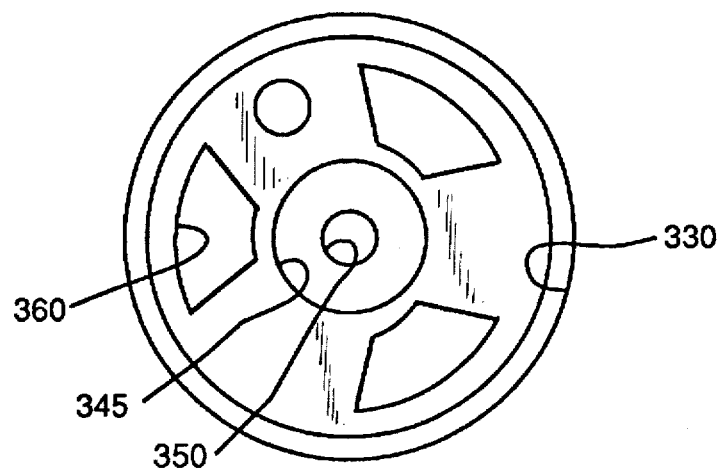
FIG. 13 is a view along section line 13—13 of FIG. 12.

Therefore, referring to FIGS. 2, 3 and 4, there is shown the subject matter of the present invention, which is an apparatus, generally referred to as 170, for removing a sample or wall portion 180 from a wall 190 of a tubular member, such as tube 50. Wall portion 180 has a distal end portion 194 and a proximal end portion 196 and may have a generally oval configuration when viewed in elevation, as best seen in FIG. 4. Of course, it will be understood with reference to the several figures, that the terminology "proximal end portion" means that end portion closer to tubesheet 90 and the terminology "distal end portion" means that end portion further away from tubesheet 90. Wall portion 180 is defined or formed by a slot 200 (exaggerated for clarity) cut through wall 190. Slot 200 circumscribes wall portion 180 in such a manner that wall portion 180 nonetheless remains suspended in and integrally attached to wall 190 by a pair of aligned hinges, tabs or ligatures 210 after completion of the cutting operation that forms slot 200. In this regard, each ligature 210 spans slot 200 and has one end portion thereof integrally attached to wall portion 180 and the other end portion thereof integrally attached to wall 190. Ligatures 210 may be colinerally aligned and disposed on either side of wall portion 180, so as to define a pivot axis 220 extending through ligatures 210. Slot 200 may be cut through tube wall 190 by operation of a suitable cutting tool (not shown), which may be an electron discharge machine. An electron discharge machine suitable for this purpose is disclosed in U.S. patent application Ser. No. 08/355,584 titled "Electron Discharge Machining Apparatus And Method" filed the same day as the present application in the name of William G. Cole, et al. and assigned to the assignee of the present invention, the disclosure of which is hereby incorporated by reference. Thus, prior to use of the present invention, such a cutting tool is disposed in tube 50 and operated therein to cut slot 200, so as to define wall portion 180 and its associated ligatures 210.

Turning now to FIGS. 3, 5, 6, 7, 8, 9 and 12, apparatus 170 comprises a probe body, generally referred to as 235, which includes displacement means, such as a generally barrel-shaped and radially expandable bladder 230. Bladder 230 has a plurality of raised spaced-apart bumps, nodules or protuberances 240 integrally formed therewith and colinerally aligned therearound. Bladder 230, which is capable of being pressurized in order to expand bladder 230, is preferably a resilient thermo-elastomer material, such as "PELLETHANE CPR-2103", available from the Upjohn Company, located in Torrance, Calif. or a suitable polyurethane of a predetermined durometer. Bladder 230 has an inside surface 250 surrounding a generally cylindrical central body 260 which supports bladder 230. Central body 260 has a flow channel 262 therethrough in communication with inside surface 250 of bladder 230. As described in more detail hereinbelow, flow channel 262 is capable of conducting an expansion fluid (e.g., a gas or liquid) to bladder 230 for expanding bladder 230. Moreover, as described in more detail hereinbelow, at least one of protuberances 240 is caused to engage and push distal end portion 194 of wall portion 180 outwardly from wall 190 as bladder 230 expands. As distal end portion 194 is pushed, it will rotate or pivot outwardly from wall 190, so that wall portion 180 pivots about pivot axis 220. As distal end portion 194 rotates outwardly from wall 190, proximal end portion 196 of wall portion 180 will rotate or pivot into the interior of tube 50. It will be appreciated from the description immediately hereinbelow, that as bladder 230 is pressurized, it will asymmetrically radially expand. This is important because as bladder 230 asymmetrically expands, protuberance 240 will engage distal end portion 194 and readily tilt window portion 180 without expanding the remaining portion of tube 50 that is in contact with bladder 230. This is so because, as bladder 230 radially expands, it will encounter the least resistance where it engages cut wall portion 180 which is suspended in wall 190 only by ligatures 210.

Referring to FIGS. 3, 6, 7, 8, 9, 10 and 11, the displacement means also includes an elongate mandrel 270 that is capable of vertically downwardly moving into intimate engagement with proximal end portion 196 of wall portion 180 after proximal end portion 196 has been pivoted into the interior of tube 50. Mandrel 270 is thereafter capable of vertically downwardly translating or displacing wall portion 180 to sever ligatures 200, as described in more detail presently. In this regard, mandrel 270 has a distal end portion 280 of predetermined transverse cross section and a proximal end portion 290 of smaller transverse cross section. Distal end portion 280 and proximal end portion 290 of mandrel 270 are integrally interconnected by a generally downwardly tapered or conically-shaped transition portion 300. It is transition portion 300 which engages proximal end portion 196 of wall portion 180 in order to downwardly (i.e., toward tubesheet 90) displace wall portion 180 a predetermined distance sufficient to sever ligatures 200. That is, as wall portion 180 is downwardly displaced, a downwardly-directed shear force acts upon ligatures 200 such that ligatures 200 are sheared or severed. Proximal end portion 290 of mandrel 270 preferably comprises three elongate legs 310 each terminating in an outwardly or radially projecting flange or foot 315 for reasons disclosed hereinbelow. Moreover, slidably extending through mandrel 270 may be a shaft 317 having sensor means, such as an eddy current sensor coil 318, connected thereto for detecting the location of wall portion 180 by sensing the presence of slot 200. Shaft 317 has an externally threaded distal end portion threadably connected to central body 260 and an externally threaded proximal end portion for reasons disclosed presently. In addition, centrally formed through shaft 317 is a channel 319 in communication with flow channel 262 which is formed in central body 260. Channel 319 receives the previously mentioned expansion fluid and conducts the fluid to channel 262 for expanding bladder 230.

Referring to FIGS. 3, 5, 6, 7, 8, 9, 12 and 13, retaining means, such as a cup-shaped retainer 320, surrounds mandrel 270 for retaining the severed wall portion 180 between mandrel 270 and retaining means 320. Retainer 320 has an open mouth portion 330 and a base portion 340. Formed through base portion 340 is a channel 350 in communication with channel 319 for conducting the expansion fluid through channel 350 and thence to channel 319. Also formed through base portion 340 are a plurality of through holes 360 for slidably receiving respective ones of legs 310. Base portion 340 also has an internally threaded recess 345 in communication with channel 350. The purpose of recess 345 is to threadably receive the externally threaded proximal end portion of shaft 317.

Referring again to. FIGS. 1, 2, 3, 5, 6, 7, 8, 9, 12 and 13, connected to mandrel 270, such as by a connector 370, is a rod 380 for reasons disclosed hereinbelow. Rod 380 has a distal end portion threadably connected to connector 370 and a proximal end portion threadably connected to movement means, such as a hydraulic or pneumatic cylinder 390, which has a passage 400 longitudinally therethrough. The purpose of pneumatic cylinder 390 is to downwardly (i.e., towards tubesheet 90) pull rod 380, which in turn downwardly translates connector 370. Rod 380 is downwardly pulled when pneumatic cylinder 390 is operated because rod 380 is threadably connected to pneumatic cylinder 390. As connector 370 is downwardly pulled, mandrel 270 is downwardly pulled to a like extent because connector 370 is connected to mandrel 270 by feet 315 that belong to legs 310 of mandrel 270. A tubular housing 410 has a distal end portion 420 connected, such as by welding, to base portion 340 of retainer 320 and a proximal end portion 430 connected, such as by welding, to an adaptor 440. Adaptor 440 has a plurality of serrations 450 on the exterior surface thereof for intimately engaging the interior surface 460 of a flexible hose 470. The purpose of housing 410 is to house and protect base portion 340, connector 370, rod 380 and pneumatic cylinder 390 from damage during the removal of wall portion 180.

Figure 14:
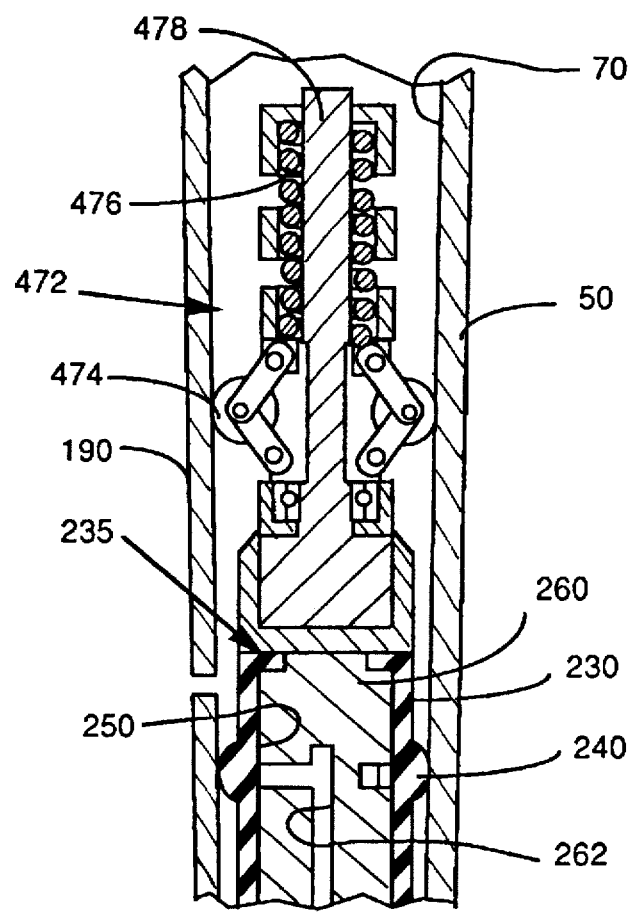
FIG. 14 is a view in vertical section of centering means belonging to the invention for centering the invention in the tube.

As best seen in FIG. 14, centering means, generally referred to as 472, is provided for centering probe body 235 in tube 50, so that the exterior of probe body 235 does not scrape inside surface 70 of tube 50 to mar inside surface 70.

It is important that probe body 235 not mar inside surface 70. This is important because marring of inside surface 70 may otherwise provide localized sites for corrosion cracking of tube 50 during operation of steam generator 10. Centering means 472 has a plurality of radially adjustable wheels 474 for adjustably engaging inside surface 70 of tube 50. Wheels 474 may be spring-biased outwardly by means of coil springs 476 that are attached to wheels 474 and that surround a central shaft 478 which is connected to central body 260.

Returning to FIGS. 1 and 2, hose 470 may be fed from about a suitable take-up reel or coiler 480 which is rotatable about a central axle 485. Extending through hose 470 is a flexible first conduit 490 which is in communication with passage 400. In fluid communication with first conduit 490 is a pressurized first fluid source 500 containing a pressurized fluid (e.g., gas or liquid) having a pressure of approximately 80 to 100 psia for supplying pressurized fluid to first conduit 490 to pressurize bladder 230. Also extending through hose 470 is a flexible second conduit 510 which is connected to pneumatic cylinder 390. In fluid communication with second conduit 510 is a pressurized second fluid source 520 for supplying fluid (e.g., gas or liquid) to pneumatic cylinder 390 in order to operate pneumatic cylinder 390. Moreover, electrically connected to sensor coil 275 is a monitor (not shown) for monitoring and displaying the output signals of sensor coil 275. In addition, engaging hose 470 is a probe pusher 530 for translating hose 470 and thus probe body 235 in tube 50.

Figure 17:
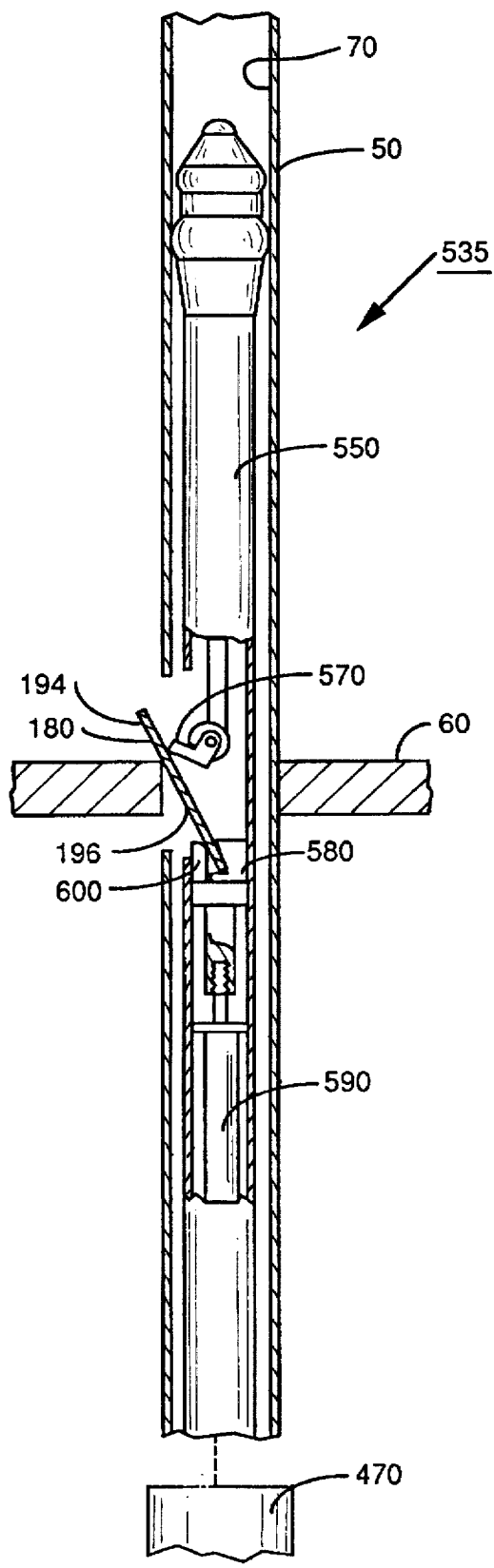
FIG. 17 is a view in partial vertical section of the alternative embodiment of the invention severing the wall portion from the wall of the tube.

Turning now to FIGS. 15, 16 and 17, there is shown an alternative embodiment of apparatus 170. This alternative embodiment of apparatus 170 comprises a probe body 535 that includes sensor means, such as eddy current coil 540 for locating slot 200. A first cylinder 550 operates an elongate plunger 560 slidably disposed therein, such that plunger 560 slidably engages a lever 570 to rotate lever 570. As lever 570 rotates, it will engage distal end portion 194 of wall portion 180 to pivot wall portion 180 about ligatures 210. A first gripper finger 580 is disposed beneath lever 570 and is vertically fixed within probe body 535. Probe body 535 also includes a hydraulic or pneumatic second cylinder 590 connected to a vertically movable second gripper finger 600 for vertically moving second gripper finger 600. Second gripper finger 600 is vertically moved after wall portion 180 pivots to capture proximal end portion 196 between fixed first gripper finger 580 and moveable second gripper finger 600. Probe body 535 is then downwardly translated to displace or downwardly translate wall portion 180 in order to sever ligatures 210.

OPERATION

Steam generator 10 is first removed from service in the manner customarily used in the art. A suitable cutting tool (not shown) is inserted into tube 50 and translated to a predetermined elevation therein, such as to the elevation of a selected support plate 60, and operated to cut slot 200 through wall 190 of tube 50. It will be understood from the description hereinabove, that after the cutting tool cuts slot 200, ligatures 210 will nonetheless remain to connect wall portion 180 to wall 190 of tube 50. After slot 200 is cut in wall 190, the cutting tool is then removed from tube 50.

Next, apparatus 170 is transported sufficiently near steam generator 10 to remove wall portion 180 from tube 50. In this regard, probe body 235 is inserted through manway 150 and into tube 50. Probe body 235 is then translated in tube 50 by operation of probe pusher 530 while sensor coil 317 is operated to detect the location of slot 200 previously cut through wall 190 of tube 50. Of course, as probe body 235 translates in tube 50, hose 470 will uncoil from about coiler 480. After wall portion 190 is located, bladder 230 is positioned thereat such that protuberance 240 is disposed adjacent distal end portion 94 of wall portion 180.

First fluid source 500 is operated to supply pressurized fluid into first conduit 490, through channel 319, through channel 262 and to the inside surface 250 of bladder 230 in order to radially expand bladder 230. Bladder 230 will asymmetrically radially expand such that at least one protuberance 240 engages distal end portion 194 of wall portion 180. As protuberance 240 engages distal end portion 194, it will push or rotate distal end portion 194 outwardly from tube wall 190 so that wall portion 180 pivots about pivot axis 220 (i.e., about ligatures 210). As wall portion 180 pivots, the proximal end portion 196 thereof will rotate or pivot inwardly into tube 50 and engage transition portion 300 of mandrel 270. After proximal end portion 196 pivots into tube 50, the fluid is drained from bladder 230 to depressurize bladder 230 by returning the fluid to first fluid source 500.

Housing 390 is then translated upwardly so that retainer 320, which is connected to the distal end portion 420 of housing 410, translates upwardly. As retainer 320 translates upwardly, mouth portion 330 thereof will engage proximal end portion 196 of wall portion 180 for retaining or gripping proximal end portion 196 between transition portion 300 and mouth portion 330.

Next, second fluid source 520 is operated to supply fluid to pneumatic cylinder 390 in order to operate pneumatic cylinder 390. As pneumatic cylinder operates, it will pull rod 380 downwardly in order to downwardly pull connector 370. As connector 370 is downwardly pulled, it will downwardly pull mandrel 270 because legs 310 of mandrel 270 are connected to connector 370 by feet 315. As mandrel 270 is pulled downwardly, legs 315 will slide through holes 360 formed through base portion 340 of retainer 320. Moreover, as mandrel 270 is pulled downwardly, shear forces acting on ligatures 210 will sever ligatures 210 for separating wall portion 180 from wall 190 of tube 50.

Probe pusher 530 is then operated to remove probe body 235 and the wall portion 180 gripped thereby from tube 50. The tube 50 may then be plugged by a suitable tube plug (not shown) or sleeved by a suitable tube sleeve (not shown) to avoid commingling the radioactive primary fluid with the nonradioactive secondary fluid during operation of steam generator 10. Typically, removal of wall portion 180 may be accomplished in approximately 15 minutes per tube not including "set-up" time.

With reference to the alternative embodiment of the invention, eddy current coil 540 is actuated as probe body is translated in tube 50 in order to locate slot 200. First cylinder 550 is then operated such that plunger 560 outwardly slidably extends to engage lever 570. As lever 570 is engaged by plunger 560, it will rotate to engage distal end portion 194 of wall portion 180 to pivot wall portion 180 about ligatures 210. Wall portion 180 is pivoted until proximal end portion 196 thereof stops against first gripper finger 580. First cylinder 550 is again operated to return or retract plunger 560 to its original position. Next, second cylinder 590 is operated to drive second gripper finger 600 vertically upwardly to grip lower portion 194 of wall portion 180 between first gripper finger 580 and second gripper finger 600. Next, probe body 535 is translated downwardly to shear ligatures 210. Probe body 535 and wall portion 180 gripped thereby are then removed from tube 50.

Apparatus 170 is removed from adjacent steam generator 10 and steam generator 10 is returned to service in the manner customarily used in the art. The wall portion 180 may then be subjected to testing and analysis to determine whether cracking of tube 50 is eminent.

Use of the present invention obviates the need to "pull" tube 50 in order to perform analysis thereon. Thus, it will be appreciated from the description hereinabove, that an advantage of the present invention is that the wall portion 180 may be removed from the wall 190 of the tube 50 in a manner that is less time consuming than the prior art tube "pull" process, that does not result in extended plant outages and that does not increase radiation exposure to service personnel. Another advantage of the present invention is that the opening left in the wall of the tube 50 after removal of wall portion 180 affords a vantage point to visually inspect the condition of neighboring tubular members before tube 50 is subsequently plugged or sleeved.

Although the invention is illustrated and described herein in its preferred embodiment, it is not intended that the invention as illustrated and described be limited to the details shown, because various modifications may be obtained with respect to the invention without departing from the spirit of the invention or the scope of equivalents thereof. For example, the invention is described herein for removal of a wall portion from a nuclear steam generator tube. However, the invention is suitable for use in removing a wall portion from any similar tube, whether or not the tube is a nuclear steam generator tube.

Therefore, what is provided are an apparatus and method for removing a wall portion from a wall of a tubular member, such as a nuclear steam generator tube, so that the tubing material thereof may be analyzed.

What is claimed is:

1. An apparatus for removing a wall portion from a wall of a tubular member, the wall portion suspended in the wall of the tubular member by a ligature thereof, comprising:

(a) displacement means for displacing the wall portion, so that the ligature severs as the wall portion is displaced; and (b) retaining means disposed adjacent said displacement means for retaining the wall portion as the ligature severs, so that the wall portion is capable of being removed from the wall of the tubular member after the ligature severs.

2. The apparatus of claim 1, further comprising pivot means engageable with the wall portion for pivoting the wall portion about the ligature and into engagement with said displacement means.

3. The apparatus of claim 2, wherein said pivot means is an expandable bladder having a protuberance thereon for pushing the wall portion to pivot the wall portion.

4. The apparatus of claim 2, wherein said pivot means is a lever for pushing the wall portion to pivot the wall portion.

5. The apparatus of claim 1, wherein said displacement means comprises a mandrel.

6. The apparatus of claim 1, wherein said retainer means comprises a retainer associated with said displacement means for retaining the wall portion between said retainer and said displacement means after the ligature severs.

7. The apparatus of claim 1, further comprising a sensor associated with said displacement means for locating the wall portion to be removed.

8. An apparatus for removing a wall portion from a wall of a tubular member, the wall portion defined by a slot cut through the wall of the tubular member and circumscribing the wall portion, such that the wall portion is suspended in the wall of the tubular member by a ligature thereof connecting the wall portion to the wall of the tubular member, the apparatus comprising:

(a) pivot means engageable with the wall portion for pivoting the wall portion about the ligature;

(b) a mandrel connected to said pivot means, said mandrel capable of moving into engagement with the wall portion after the wall portion pivots and thereafter capable of displacing the wall portion to sever the ligature; and (c) a retainer surrounding said mandrel for retaining the wall portion between said retainer and said mandrel.

9. The apparatus of claim 8, wherein said pivot means is an expandable bladder having a protuberance thereon for pushing the wall portion as the bladder expands, so that the wall portion pivots about the ligature.

10. The apparatus of claim 8, wherein said pivot means is a rotatable lever for pushing the wall portion as the lever rotates, so that the wall portion pivots about the ligature.

11. The apparatus of claim 8, further comprising an eddy current sensor associated with said mandrel for locating the wall portion to be removed.

12. For use in a nuclear steam generator tube, an apparatus for removing a wall portion from a wall of the tube, the wall portion defined by a slot cut through the wall of the tube and circumscribing the wall portion, such that the wall portion is suspended in the wall of the tube by a pair of ligatures thereof connecting the wall portion to the wall of the tube, the ligatures being colinerally aligned to define a pivot axis extending therethrough, the wall portion having a distal end and a proximal end, the apparatus comprising;

(a) pivot means engageable with the wall portion for pivoting the wall portion about the ligatures;

(b) an elongate mandrel connected to said pivot means, said mandrel capable of moving into intimate engagement with the proximal end of the wall portion after the wall portion pivots and thereafter capable of moving to displace the wall portion as said mandrel engages the proximal end of the wall portion in order to sever the ligatures; and (c) a cup-shaped retainer surrounding said mandrel for retaining the wall portion between said retainer and said mandrel after the ligatures sever.

13. The apparatus of claim 12, wherein said pivot means comprises a radially expandable bladder sized to be disposed in the tube, said bladder having a plurality of spaced-apart protuberances integrally formed therewith and colinerally aligned therearound for pushing the distal end of the wall portion as the bladder expands, so that the wall portion pivots about the pivot axis to rotate the proximal end of the wall portion into the tube.

14. The apparatus of claim 12, wherein said pivot means comprises a rotatable lever for pushing the wall portion as the lever rotates, so that the wall portion pivots about the ligature.

15. The apparatus of claim 12, further comprising an eddy current sensor connected to said mandrel for locating the wall portion to be removed.

16. A method of removing a wall portion from a wall of a tubular member, the wall portion suspended in the wall of the tubular member by a ligature thereof, comprising the steps of:

(a) displacing the wall portion, so that the ligature severs as the wall portion is displaced; and (b) retaining the wall portion as the ligature severs.

17. The method of claim 16, further comprising the step of pivoting the wall portion about the ligature prior to displacing the wall portion.

18. The method of claim 17, wherein said step of pivoting the wall portion comprises the step of pushing the wall portion by expanding a bladder having a protuberance thereon into engagement with the wall portion.

19. The method of claim 18, further comprising the step of locating the wall portion to be removed by operating an eddy current sensor associated with the mandrel.

20. The method of claim 16, wherein said step of displacing the wall portion comprises the steps of:

(a) moving a mandrel into engagement with the wall portion after pivoting the wall portion; and (b) moving the mandrel to displace the wall portion after moving the mandrel into engagement with the wall portion.

21. The method of claim 16, wherein said step of retaining the wall portion comprises the step of retaining the wall portion between the mandrel and a retainer surrounding the mandrel.

22. The method of claim 16, further comprising the step of locating the wall portion to be removed by operating a sensor associated with the mandrel.

23. In a nuclear steam generator tube, a method of removing a wall portion from a wall of the tube, the wall portion defined by a slot cut through the wall of the tube and circumscribing the wall portion, such that the wall portion is suspended in the wall of the tube by a pair of ligatures thereof connecting the wall portion to the wall of the tube, the ligatures being colinerally aligned to define a pivot axis extending therethrough, the wall portion having a distal end and a proximal end, the method comprising the steps of:

(a) pivoting the wall portion about the pivot axis by radially expanding a bladder having a plurality of spaced-apart protuberances integrally formed therewith and colinerally aligned therearound, at least one of the protuberances pushing the distal end of the wall portion as the bladder expands in order to rotate the proximal end of the wall portion into the tube as the wall portion pivots;

(b) moving an elongate mandrel into intimate engagement with the proximal end of the wall portion after pivoting the wall portion;

(c) moving the mandrel to downwardly displace the wall portion after moving the mandrel into engagement with the wall portion in order to sever the ligatures; and (d) retaining the wall portion between the mandrel and a cup-shaped retainer surrounding the mandrel after the ligatures sever.

* * * * *